United States Patent [19]
Appleton

[11] Patent Number: 5,234,840
[45] Date of Patent: Aug. 10, 1993

[54] ASSAY WITH BACKWASH

[75] Inventor: Peter N. Appleton, Huntingdon, United Kingdom

[73] Assignee: Porton Cambridge Limited, Kennett, England

[21] Appl. No.: 325,784

[22] Filed: Mar. 20, 1989

[30] Foreign Application Priority Data

Mar. 31, 1988 [GB] United Kingdom ............... 8807698

[51] Int. Cl.$^5$ ............................................ G01N 33/543
[52] U.S. Cl. ..................................... 436/518; 422/58;
436/165; 436/501; 436/528; 436/538; 436/805;
436/810; 436/530
[58] Field of Search ............... 436/518, 538, 528, 165,
436/810, 805, 530; 422/58, 57, 61, 101

[56] References Cited

U.S. PATENT DOCUMENTS

| 3,733,179 | 5/1973 | Guehler et al. | 436/165 |
|---|---|---|---|
| 4,016,043 | 4/1977 | Schuurs et al. | 195/103.5 R |
| 4,168,146 | 9/1979 | Grubb et al. | 23/230 B |
| 4,200,690 | 4/1980 | Root et al. | 436/528 |
| 4,497,900 | 2/1985 | Abram et al. | 436/511 |
| 4,632,901 | 12/1986 | Valkins et al. | 435/5 |
| 4,790,857 | 12/1988 | Miksch | 422/61 |
| 4,874,691 | 10/1989 | Chandler | 422/58 |
| 4,889,812 | 12/1989 | Guinn et al. | 435/285 |
| 4,912,034 | 3/1990 | Kalra et al. | 422/58 |

FOREIGN PATENT DOCUMENTS

| 0093613 | 11/1983 | European Pat. Off. . |
|---|---|---|
| 0198413 | 10/1986 | European Pat. Off. . |
| 0258963 | 3/1988 | European Pat. Off. . |
| 0272044 | 6/1988 | European Pat. Off. . |
| 1420916 | 1/1976 | United Kingdom . |
| 1489913 | 10/1977 | United Kingdom . |
| 1502563 | 3/1978 | United Kingdom . |
| 1522567 | 8/1978 | United Kingdom . |

OTHER PUBLICATIONS

Kohler, *Antigen Detection to Diagnose Bacterial Infections*, Boca Raton, Fla.: CRC Press, Inc., 1986, pp. 73-75.

*Primary Examiner*—David Saunders
*Assistant Examiner*—Christopher L. Chin
*Attorney, Agent, or Firm*—Lee, Mann, Smith, McWilliams, Sweeney & Ohlson

[57] ABSTRACT

A method of, apparatus for and test kit for determining the presence of an analyte in a sample during an immunoassay, wherein the sample is contacted with a porous carrier carrying, an immobilized form on its surface, a binding partner for the analyte of interest, the carrier is backwashed to remove unbound material at said surface, and the presence of analyte bound to the carrier surface is determined.

10 Claims, 1 Drawing Sheet

ASSAY WITH BACKWASH

FIELD OF INVENTION

This application relates to an assay technique based on the affinity of an analyte for binding partner, such as antigen-antibody affinity, and concerns a method, apparatus and test kit for use in determining the presence of an analyte in a sample.

BACKGROUND TO THE INVENTION

In medical and other fields, a common way of detecting an antigen, antibody, or other analyte of interest is to utilise a specific or nonspecific binding partner or capture agent bound to, or immobilised, on a solid support. The sample potentially containing the analyte of interest is then brought into contact with the supported capture agent. After a period for reaction, a further, detecting reagent is added. This second reagent may be added before or after washing the solid support free of unbound sample. After a further reaction period to enable the detecting reagent to react with the analyte already reacted with, and bound to, the capture agent on the solid phase support, all unreacted material is removed from the site of reaction. In the final step, a process designed to reveal a label characteristic of the detecting reagent is used to reveal the presence of the detecting reagent bound to the analyte which in turn is bound to the capture agent on the solid phase support. The specificity of the result is conferred by the specificity of either or both of the capture and detecting reagents for the analyte.

The solid phase may be plastics, glass, metal, paper or porous membrane in any desired shape or size.

The capture agent may be antigen, antibody, lectin or other reagent having a reaction with the analyte of interest.

The detecting reagent may be antigen, antibody, lectin or other reagent having the capability of binding to the analyte, and labelled with an enzyme, radioisotope, fluorophore or heavy metal compound or other molecule or atom which may subsequently be detected with convenience to the user.

Such tests are frequently performed using a porous membrane or paper as the solid support. Sample, washing fluid and other reagents are added in sequence, each one passing through the membrane into a void space or absorbent material on the side of the membrane distal to the site of the reactions.

This method of performing the test is limited to samples which are either free of material of such a size as to block the pores of the membrane, or have been rendered free of such material by a procedure such as filtration or centrifugation, since blocked pores will inhibit the flow of washing fluids. The final step of detecting specifically-bound label will then be rendered very difficult because of the amount of unbound label remaining.

The present invention aims to provide an improvement to such methods.

SUMMARY OF THE INVENTION

According to one aspect of the present invention there is provided a method of determining the presence of an analyte in a sample, comprising contacting the sample with a surface of a porous carrier on which is immobilised a binding partner to the analyte of interest so that analyte, if any, in the sample binds to the immobilised binding partner; passing washing fluid through the carrier so as to emerge from said surface to remove unbound material; and determining the presence of analyte bound with respect to said surface.

Washing the carrier surface with fluid passed through the carrier is an efficient and effective way of removing unwanted, unbound material that would otherwise hinder accurate determination of bound material. In consequence, the method of the invention finds particular, but not exclusive, application for samples containing materials that would otherwise block the carrier pores, including, e.g., faecal, sputum and other 'dirty' biological fluid samples.

The method of the invention is applicable e.g. to immunoassays, with the analyte comprising an antigen or antibody and the binding partner being the corresponding antibody (monoclonal or polyclonal) or antigen. The presence of bound analyte can be determined in a conventional manner, as is known to those skilled in the art, such as by a sandwich assay technique using a detecting reagent which binds to the immobilised analyte and which carries a detectable label. The label may comprise, e.g., an enzyme, radioisotope, fluorophore or heavy metal compound which can be detected in a known manner. It is preferred to use a label that produces a visible change detectable by the naked eye, e.g. an enzyme-catalysed colour change. A suitable labelled reagent may be added before or after the washing step: the order of these steps is not critical. After washing an appropriate procedure is carried out to reveal the particular label used: for example where the label is an enzyme a reagent which produces an enzyme-catalysed colour change may be added; a radiation detector may be used to reveal a radioisotope label; a fluorimeter may be used to reveal flourophore label; a heavy metal label such as colloidal gold may be visualised by silver staining etc.

The method may be used qualitalively or quantitatively (by comparison with results from known standards).

The washing fluid conveniently comprises buffered saline solution, e.g. 0.1 molar phosphate-buffered saline, pH 7.3, possibly containing 0.1% v/v Tween 20 detergent (Tween is a Trade Mark).

The washing fluid is desirably forced through the porous carrier, e.g. by being squeezed from a deformable container such as a plastic bottle.

The porous carrier conveniently comprises porous plastic material. The presently preferred material is activated nylon e.g. Immunodyne 1 from Pall (Europe) Ltd: the binding partner binds covalently to such activated material, and a high density of covalently bound binding partner can be obtained. Many other carrier materials can also be used including e.g. nitrocellulose membranes or polyurethane membranes (e.g. grade HPI from Amicon Corporation): such materials are non-activated and bind by non-convalent or physical trapping mechanisms.

The carrier is preferably of planar configuration, e.g. in the form of a disc, with immobilised binding partner on one planar face.

The binding partner may be immobilised on the surface of the porous carrier in a conventional manner, as is known to those skilled in the art, e.g. by covalent linking. Any remaining active sites on the carrier surface may be "blocked" in a conventional manner to prevent non-specific binding, e.g. by application of solution of defatted milk.

A sheet of filter paper of similar material is desirably located adjacent the porous carrier, remote from the surface bearing immobilised binding partner, i.e. upstream of the direction of flow of washing fluid to spread the washing fluid across the extent of the carrier.

The porous carrier is conveniently located in the neck of a container of washing fluid, with a reaction space for receiving a sample to be tested defined above the binding partner-bearing surface of the carrier.

Hence in a further aspect of the present invention provides apparatus for use in determining the presence of an analyte in a sample, comprising a container divided by a porous carrier into a first, generally enclosed part for containing washing fluid and a second part constituting a reaction space for receiving a sample to be tested, the porous carrier having immobilised on the surface adjacent said second part a binding partner to the analyte.

In use, suitable washing fluid is located in the first part of the container. A sample is added to the second part of the container, to contact the binding partner-bearing surface of the carrier. After a suitable reaction time the container in inverted and washing fluid expelled from the first part to pass through the carrier and remove any unbound, unwanted material: such material is allowed to flow into a receptacle for disposal in suitable manner. The presence of analyte bound with respect to the carrier surface is then determined as described above: for example, labelled detecting reagent may be added to the reaction space (before or after washing), and a suitable label revealing procedure carried out after washing, e.g. by addition of a suitable reagent to the reaction space after re-inversion of the container.

The first part of the container is preferably constituted by a deformable plastics bottle with a removable stopper so that washing fluid can be sealed in the bottle for storage and expelled by squeezing when required. The porous carrier is preferably located in a holder adapted to be removably fitted in the neck of such a bottle on removal of the stopper. Such a holder and carrier can be packed separately from the bottle, e.g. in an airtight, moisture free container, to maintain the immobilised binding partner in good condition during storage, with the holder being fitted into the bottle neck when required for use. The holder preferably comprises male and female parts with the porous carrier firmly held therebetween.

In another aspect the present invention provides a test kit for use in determining the presence of an analyte in a sample, comprising a container of washing fluid; and a holder adapted to be fitted into the neck of the container and bearing a porous carrier with binding partner to the analyte immobilised on a surface of the carrier.

The kit may also include a supply of appropriate reagents such as labelled detecting reagent, and possibly also enzyme substrate if appropriate.

Reagents may conveniently be supplied in air-dried form on a carrier of porous insoluble material from which the reagent is substantially fully recoverable into solution.

The kit may also include controls of known concentration of the analyte of interest for comparison purposes.

The invention may be used for determination of a wide range of analytes, including any virus, bacterium, fungus or parasite; their antigens, excretions and secretions; hormones; antibodies of any known immunoglobulin class; or any molecule having at least two sites to which capture and detecting agents can bind.

Tests envisaged in this format include tests for infection with:
Rotavirus
  *Giardia lamblia*
  *Entamoeba histolytica*
  *Neisseria gonorrhoeae*
  *Chlamydia* spp.
  Shigella spp.
  Salmonella spp.
  *Vibrio cholerae* and related Vibrio spp.
  Enterotoxins
Influenza viruses
Parainfluenza viruses
Respiratory syncytial virus
Adenoviruses
Herpes viruses
  *Streptococcus pneumoniae*
  *Mycoplasma pneumoniae*
  *Streptococcus pyogenes*
  *Mycobacterium tuverculosis*
  *Neisseria meningitidis*
  Candida spp.
  *Trichomonas vaginalis*

The invention may also be embodied as a pregnancy test, by testing for the presence of the hormone human chorionic gonadotrophin.

The invention will be further described by way of example, with reference to the accompanying drawings, in which:

DETAILED DESCRIPTION OF THE DRAWINGS

A test kit in accordance with the invention comprises the following components:

1. A bottle 10 (FIG. 1) of deformable plastics material, preferably low-density polyethylene, having an externally threaded neck for a screw cap (not shown). The bottle has a capacity of 7 milliliters, and contains 3.5 milliliters of a buffered saline solution 12. The internal surface of the bottle neck includes a circumferential recess 14 the purpose of which will be described below. For storage purpose, the bottle is sealed with a screw-cap.

Figure 2:
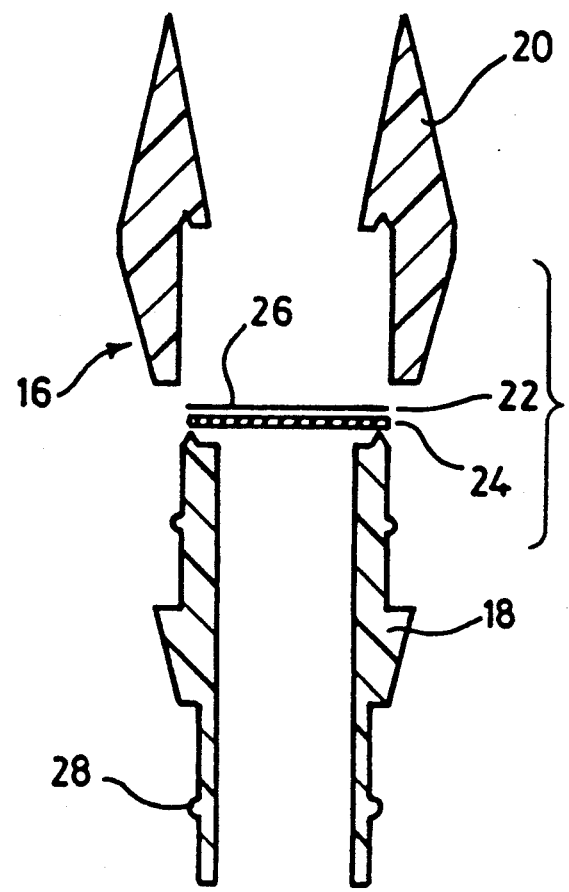
FIG. 2 is an exploded view, to an enlarged scale, of part of the apparatus shown in FIG. 1.

2. A generally tubular holder 16 (FIG. 2) of plastics material, preferably injection-moulded high-density polyethylene. The holder comprises a lower, male portion 18 and an upper, female portion 20 which are adapted to be held together by a tight push-fit relationship and to hold firmly therebetween a porous carrier 22 and a disc of fliter paper 24 (Whatman No 1). The carrier comprises a disc 12 mm in diameter of porous plastics material, preferably an activated nylon material know as Immunodyne 1 obtained from Pall (Europe) Ltd. A central area of the surface 26 of carrier 22 remote from filter paper 24 bears irreversibly covalently linked binding partner to an analyte of interest, with the remaining active sites on the carrier being "blocked" with a solution of defatted milk to prevent non-specific binding.

The lower part of male portion 18 is dimensioned to be a tight push fit in the neck of bottle 10, and this part includes a circumferential protrusion 28 adapted to be received in recess 14 to provide a sealing fit between the bottle and holder. The assembled holder, with carrier and filter paper disc, is dried and stored in an airtight container containing a dessicant such as silica gel until required for use.

3. A supply of porous plastic discs 6 millimeters in diameter, preferably of sintered poylethylene, on each of which has been air-dried a predetermined amount of a labelled detecting reagent e.g. an antibody of chosen specificity conjugated (=labelled) with an enzyme (preferably horseradish peroxidase). The conjugate carrier discs are stored in an airtight container containing a desiccant such as dry silica gel.

4. Where appropriate a reagent for revealing the label of the detecting reagent. For example, where the label comprises horseradish peroxidase, the reagent comprises a solution of hydrogen peroxide of predetermined concentration in a bottle having the capability of delivering its contents dropwise, and a similar bottle containing a solution of a predetermined concentration of 3, 3', 5, 5'- tetramethylbenzidine dihydrochloride in water.

Figure 1:
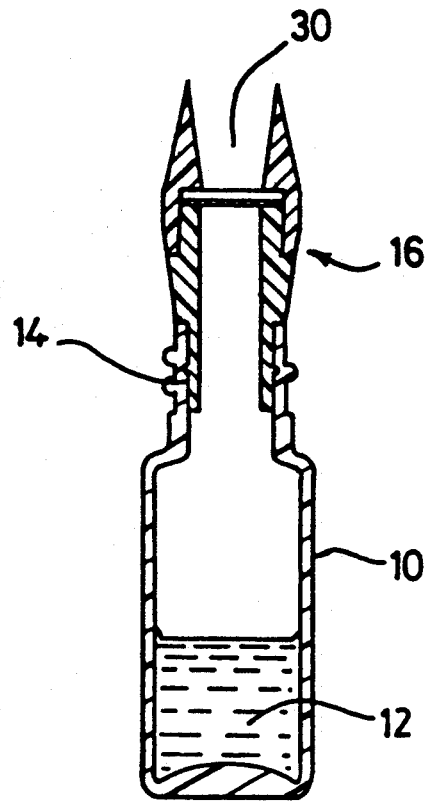
FIG. 1 is a cross section of one embodiment of apparatus in accordance with the invention.

In use, holder 16 is removed from its container, and push fitted into the neck of bottle 10 to provide a tight sealing fit, such that the holder is not displaced when the bottle is squeezed. The resulting arrangement is illustrated in FIG. 1.

A predetermined volume of a sample to be tested is located in a receptacle, to which is added a conjugate carrier as discussed in (3) above. The receptacle is securely capped and the contents mixed vigorously. The detecting reagent is substantially fully released into solution.

A predetermined volume of the resulting mixture is added to reaction space 30 (FIG. 1) defined in holder 16 above carrier 22 and allowed to stand for a suitable reaction time. During this time any analyte of interest in the sample binds to the immobilised binding partner on the corner surface 26.

After the reaction time, the bottle/holder assembly is inverted over a container of disinfectant and the bottle squeezed to force the washing fluid through the filter paper disc 24 and carrier 22, the filter paper disc acting to spread the washing fluid across the width of the carrier. The bottle is squeezed until no more fluid can be expressed. The bottle/holder assembly is returned to an upright position and allowed to regain its original shape. The disinfectant and washed off sample are disposed of carefully.

Any analyte bound to the carrier is then determined in appropriate manner, e.g. by dropwise addition of reagents as discusssed in (4) above.

The invention is further illustrated by the following Examples.

EXAMPLE 1

A test for the detection of rotavirus was constructed as follows.

Carrier holders 16 were constructed as described above the centres of the exposed upper surfaces of each carrier 22 being loaded with 2 microliters of a solution containing 0.2 mg/ml rabbit anti-rotavirus immunoglobulin. This was dried for 10 minutes in a stream of warm air, and 100 microliters of a 1% w/v solution of dried defatted milk applied and dried in a similar fashion.

The narrow ends of the holders 16 were pushed into the necks of polyethylene bottles 10 containing 3.5 milliliters each of 0.1 molar phosphate-buffered saline, pH 7.3 containing 0.1% v/v Tween 20 detergent.

10 microliters of a 1 in 20 dilution of horseradish peroxidase-conjugated rabbit antirotavirus immunoglobulin were applied to each of several 6 millimeter diameter discs of sintered polyethylene cut from 2 millimeter thick sheet. These were dried in a stream of warm air, and the resulting conjugate carriers stored in an airtight container over silica gel.

Two samples of human faeces were obtained. One shown to contain rotavirus by electron microscopy was designated POSITIVE. The other contained no demonstrable rotavirus and was designated NEGATIVE.

From each of the two samples, a suspension of approximately 10% solid matter was made in a buffered saline solution. To 1 milliliter of each suspension, a loaded conjugate carrier was added. The containers were securely capped, and the contents mixed vigorously. Approximately 400 microliters of each mixture was added to the reaction space 30 of a separate carrier holder, and the holder/bottle assemblies were allowed to stand for 10 minutes.

After the standing period, the assemblies were inverted over a container of disinfectant and the bottles squeezed until no more fluid could be expressed. The assemblies were then returned to the upright position and the bottles allowed to regain their original shape.

To the exposed carrier surface in each holder was then added in rapid sequence 1) two drops of 1 in 10,000 dilution of a 30% w/v solution of hydrogen peroxide in 0.1 molar citrate buffer, pH 6.4, and 2) two drops of approximately 50 microliters each of 3,3',5,5', tetramethylbenzidine hydrochloride at 1 milligram per milliliter in distilled water.

The carriers were observed for three minutes. In the carrier to which had been presented the POSITIVE sample a blue dot appeared, corresponding in position to the area which had been loaded with immunoglobulin. In the carrier to which had been added the NEGATIVE sample no such dot appeared.

It was concluded that since the only known difference between the samples was the presence of rotavirus the appearance of the blue dot was related to the presence of the virus in the sample, and that the method described and the kit of parts used constituted a suitable method for the testing for the presence of rotavirus in human faeces.

EXAMPLE 2

A further experiment was performed using the same procedure on 20 samples of human faeces. The same samples were also tested using a commercially available, microtitration-plate based enzyme immunoassay (International Diagnostic Laboratories, Ltd, Jerusalem). The results are given below.

| Sample No. | IDL Test Result | Membrane Test Result |
|---|---|---|
| 1. | + | + |
| 2. | + | + |
| 3. | − | − |
| 4. | − | − |
| 5. | − | − |

-continued

| Sample No. | IDL Test Result | Membrane Test Result |
| --- | --- | --- |
| 6. | + | + |
| 7. | − | − |
| 8. | + | + |
| 9. | − | − |
| 10. | − | − |
| 11. | − | − |
| 12. | − | − |
| 13. | + | + |
| 14. | − | − |
| 15. | − | − |
| 16. | − | − |
| 17. | + | + |
| 18. | − | − |
| 19. | − | − |
| 20. | − | − |

(Where "+" signifies development of visible colour)

EXAMPLE 3

A further experiment was performed exactly as described in 1. above except that the binding partner and detecting antibodies were prepared from the serum of a rabbit which had been immunised with the trophozoites of *Giardia lamblia (Giardia intestinalis)*. The test was performed in the same way as above, save that the incubation time was increased to 20 minutes after presentation of the mixture of sample and enzyme-conjugated antibody to the carrier.

Results. All of five samples known to contain the trophozoites of *Giardia lamblia* were shown to yield central blue dots on the loaded carriers. All of 10 samples in which the trophozoites were not detectable by microscopy showed no blue dots.

EXAMPLE 4

A further experiment similar to those above was performed using rabbit antibodies to *Herpesvirus hominis* (herpes simplex virus) on the carrier and the same antibodies conjugated to peroxidase as detecting reagent. In this case, the Positive sample used was a fluid extract of a cell culture supporting the multiplication of a strain of *Herpesvirus hominis*. The incubation period was once again limited to 10 minutes.

Results. The test done on a sample known to contain the virus yielded a central blue dot on the carrier. A test run simultaneously with an extract of a cell culture containing no virus showed an absence of blue coloration.

I claim:

1. A method of determining the presence of an analyte in a sample, comprising the steps of:
    (a) providing an apparatus comprising a container divided by a porous carrier into a first enclosed part for containing a wash fluid and a second part constituting a reaction space for receiving the sample to be tested, said porous carrier comprising a first surface facing said reaction space with an immobilized binding partner to the analyte and a second surface opposite said first surface facing the enclosed part of the container;
    (b) contacting the sample with the first surface of the porous carrier so that analyte in the sample binds to the immobilized binding partner, and passing the sample through the porous carrier so as to emerge from the second surface of the porous carrier into said first enclosed part of the container;
    (c) inverting the apparatus to apply the was fluid to said second surface of the porous carrier so as to pass said wash fluid through the porous carrier in a direction opposite to that in which the sample passes so that wash fluid emerges from said first surface of the porous carrier to remove unbound material;
    (d) contacting the first surface of said porous carrier with a detecting reagent which binds specifically to the analyte, wherein said detecting reagent carries a detectable label; and
    (e) determining the presence of detectable label on the first surface of the porous carrier and relating the presence of said detectable label to the presence of analyte in the sample.

2. A method according to claim 1, wherein the analyte comprises an antigen and the binding partner is an antibody which binds specifically to the antigen.

3. A method according to claim 2, wherein the presence of bound analyte is determined by a sandwich assay technique using a detecting reagent which binds specifically to the immobilized analyte and which carries a detectable label.

4. A method according to claim 1, wherein the wash fluid comprises buffered saline solution.

5. A method according to claim 1, wherein the wash fluid is forced under pressure through the porous carrier.

6. A method according to claim 1, wherein the porous carrier comprises porous plastics material and is of planar configuration, with the immobilised binding partner on one planar face.

7. A method according to claim 1, wherein the binding partner is covalently linked to the porous carrier, any remaining active sites on the carrier surface being blocked to prevent non-specific binding.

8. A method according to claim 1, wherein a sheet of filter paper is located beneath the porous carrier, remote from the surface bearing immobilised binding partner, to spread the washing fluid across the extent of the carrier.

9. A method according to claim 1, wherein the binding partner comprises an antigen and the analyte is an antibody which binds specifically to the antigen.

10. A method according to claim 9, wherein the presence of bound analyte is determined by a sandwich assay technique using a detecting reagent which binds specifically to the immobilized analyte and which carries a detectable label.

* * * * *